United States Patent [19]

Aubert

[11] 4,048,308
[45] Sept. 13, 1977

[54] ACELLULAR PLANKTONIC PRODUCT, METHOD OF PREPARING SAME AND COSMETIC COMPOSITION CONTAINING THE SAME

[75] Inventor: Lucien Paul Aubert, Nice, France

[73] Assignee: L'Oreal, Paris, France

[21] Appl. No.: 597,571

[22] Filed: July 21, 1975

[30] Foreign Application Priority Data

July 24, 1974 Luxembourg .......................... 70601

[51] Int. Cl.$^2$ ............................................. A61K 35/78
[52] U.S. Cl. ........................................ 424/195; 424/95
[58] Field of Search ................................. 424/95, 195

[56] References Cited

FOREIGN PATENT DOCUMENTS 2,053,399   4/1971   France ................................... 424/95

OTHER PUBLICATIONS

Chemical Abstracts, vol. 81 (1974): items 87593g; 87647k and 87648m.

*Primary Examiner*—Donald B. Moyer
*Attorney, Agent, or Firm*—Cushman, Darby & Cushman

[57] ABSTRACT

An acellular planktonic product comprises plankton, the cellular membranes of which have been ruptured. This product is usefully employed in the production of cosmetic compositions for application to human skin.

8 Claims, No Drawings

ACELLULAR PLANKTONIC PRODUCT, METHOD OF PREPARING SAME AND COSMETIC COMPOSITION CONTAINING THE SAME

The present invention relates to an acellular planktonic product, its preparation from plankton and particularly from spa-plankton, and to its use in a cosmetic composition.

It is known that planktonic products, and principally planktons obtained from sulfurous spa, have interesting dermotologic properties which have led to their use in cosmetic or hygienic compositions for the skin.

French Pat. No. 1,106,017 describes a process for cultivating and harvesting plankton which yields the latter in a quantity sufficient for cosmetic usage. This patent, however, discloses that plankton exhibits very great instability and recommends the stabilization of plankton by the addition thereto of an antiseptic agent such as phenol.

Further, French Pat. Nos. 1,372,620 and 1,536,017 propose submitting plankton to acid lysis or to various enzymatic lyses for the dual purpose of destroying the cellular membrances of bacteria and microscopic algae which constitute the plankton, and of freeing the basic amino acids present in plankton in the form of polypeptides.

However, the applicant has discovered that the cellular membrances of the constituents of plankton have in certain cases an advantageous cosmetic effect on human skin, in particular in the area of water retention which produces on the skin an emollient or softening effect.

Thus the present invention is particularly related to a planktonic product which is provided in an acellular form and which is obtained by rupturing cellular planktonic membrances.

The present invention also relates to a process for treating plankton which simultaneously frees the cytoplasmic components thereof which exhibit advantageous cosmetic properties and preserves the integrity of the chemical constitution of the cellular membranes. This process thus provides a planktonic product which is ideally useful in cosmetic compositions and which can include the fractured cellular membranes.

The process of the present invention comprises physically rupturing the planktonic cellular walls. Appropriate means for physically rupturing these cellular membrances include both mechanical and thermal means.

More specifically, the cellular membranes of plankton can be ruptured by submitting the plankton to elevated pressure in a mechanical press, or to a grinding operation in the presence of an abrasive material such as finely powdered glass or aluminum, or to a succession of severe freezings and thawings or to the repeated action of ultrasonic vibrations.

The starting material is principally freshly gathered or harvested spaplankton, or chemically stabilized plankton or frozen plankton that one has thawed at the moment of applying thereto one of the particular processes defined above. When the process employed involves grinding the plankton in the presence of abrasives, or disintegrating the plankton cellular membranes by ultrasonic vibrations, the starting spaplankton can be diluted in water such as spa-water, or with a buffered solution having an ionic strength and pH essentially the same as the spa-water. The quantity of dilution water can vary, for example between 0.1-2 times the weight of drained plankton.

When the starting plankton is frozen, it is preferably obtained in the following manner: after collecting the same, the plankton is drained by introduction into a fine mesh net made, for instance, from silk, so as to eliminate most of the water. The cellular mass obtained is introduced into sterile containers and rapidly frozen, preferably at a temperature between $-35°$ and $-70°$ C. The thus frozen plankton is then heated to a temperature in the order of $-20°$ to $-25°$ C, for example $-23°$ C. Plankton at this temperature can be stored for a long time. This preservation process avoids the inconvenience of employing a preservative agent so as to stabilize the plankton after its collection or harvesting.

The following illustrates preferred operating methods:

When grinding the plankton with an abrasive, the abrasive is, for example, very finely powdered glass or aluminum; the grinding is effected for example in a motor actuated pestle; after grinding the acellular extract is separated from the abrasive by decantation;

When rupturing the cellular membranes of plankton by means of a mechanical press, the plankton is submitted to elevated pressures ranging between about 500 and 1500 kg/cm$^2$ and the press liquid is then recovered;

when disintegrating the cellular membranes of plankton with ultrasonic vibrations, repeated impulses of a frequency ranging between about 15 and 20 kilocycles are applied to the plankton. Preferably from 10 to 20 impulses of a duration of 20 to 40 seconds are applied to the plankton. To prevent alteration of certain thermolabile active compounds, the container housing the plankton is provided with a cooling system;

When submitting the plankton to a succession of severe freezings and thawings, the freezings are effected by cooling the plankton to a temperature between $-20°$ and $-70°$ C. This operation is repeated, for example, from 2–15 times, preferably from 8 to 10 times.

Each of the above described procedures of the present case yields either an acellular solution or an acellular suspension in which are present both a ruptured membrane fraction and the cytoplasmic components which had been contained in the unruptured membranes. The chemical constitution of these cytoplasmic components is essentially the same as that of said components in the biologic state, or very close thereto.

The membrance fraction contained in the resulting planktonic product can be separated, if desired, by means of conventional separation techniques, particularly such as a differential centrifugation operation.

Accordingly, the present invention relates principally to an acellular planktonic product obtained by anyone of the processes described above.

The present invention also relates to the cosmetological use of the above defined acellular planktonic product.

The present invention also relates to the use of said acellular planktonic product by incorporating the same into a cosmetic or hygienic composition for topical application to human skin.

The present invention further relates to a cosmetic composition for topical application to human skin comprising an acellular planktonic product defined above.

The cosmetic composition of the present invention is principally a transparent solution or emulsion of the lotion type; or an emulsion having a liquid or semi-liquid consistency such as a milk-type composition which can be obtained by dispersing an oily phase in an aqueous phase, or vice versa; or a suspension or emulsion having the soft consistency of a cream type composition.

The cosmetic compositions of the present invention can contain, in addition to the said acellular planktonic product, components conventionally employed in cosmetic compositions such as perfumes, preservative agents, emulsifying agents, liquid carriers such as water and fatty bodies such as natural or synthetic oil which can comprise the oily phase of the milk-or cream-type compositions of this invention.

In the cosmetic compositions of this invention, the concentration of the acellular planktonic product can vary, of course, depending on the effect desired as well as on the particular type of composition into which it is incorporated. Generally, the acellular plantonic product is present in an amount ranging between 0.3 and 1 percent by weight (dry basis) relative to the total weight of the composition.

The pH of the cosmetic composition of the present invention can vary between about 3.5 and 8.

The acellular planktonic product in the form of a solution or suspension, optionally diluted, can be incorporated directly in the cosmetic preparations of the invention, principally those of the lotion or milk types. Additionally the acellular planktonic product can be lyophilized and coated with a fatty body such as lanolin to preserve the same and/or for introduction into cream type cosmetic compositions.

The following non-limiting examples illustrate the present invention. Unless otherwise stated, all parts and percentages are by weight.

EXAMPLES OF PREPARATION

EXAMPLE 1 — Grinding in the presence of an abrasive 1 liter of stabilized spa-plankton, or alternatively 300–350 g of thawed, drained plankton, diluted in 600–700 cc of a buffered solution of ionic strength and pH identical to the spa-water, is introduced in a mortar provided with an electric motor actuated pestle. Grinding of the plankton is effected in the presence of an abrasive such as finely powdered glass or finely powdered aluminum for 15 to 20 minutes.

After grinding, the resulting solution containing the acellular extract of plankton is separated from the abrasive material by decantation.

EXAMPLE 2 — Disintegration using ultrasonic vibrations 100 cc of stabilized spa-plankton, or alternatively 30–40 g of thawed plankton, diluted in 50 to 60 cc of a buffered solution as defined in Example 1, are introduced into a chamber of an ultrasonic disintegrator of the Branson Sonifier type, sold by Measuring and Scientific Equipment, Ltd. Crawley, Sussex, England. There are applied thereto in a period of 30 seconds, 16 impulses of a frequency in the order of 20 kilohertz, the power applied varying between 100 and 300 watts. The chamber is equipped with a continuous cooling system. This procedure yields a suspension of warm acellular planktonic product.

EXAMPLE 3 — Rupture of cellular planktonic membranes with high pressure.

Into the chamber of a press of the "Franch Press" type there are introduced 50 cc of stabilized spa-plankton or alternatively 15–20 g of plankton thawed under the same conditions given above. The plankton is then subjected to a pressure of about 1000 kg/cm$^2$, yielding as the run-off press liquid an acellular solution of plankton.

EXAMPLE 4 — Rupture of cellular plankton membranes by successive freezings and thawings 1 kg of frozen spa-plankton is permitted to thaw at ambient temperature. Thereafter the thus thawed plankton is refrozen at a temperature of about −25° C, and then again permitted to thaw at ambient temperature. This freeze-thaw operation is repeated 8 times in succession, yielding a suspension of warm acellular plankton.

EXAMPLES OF COSMETIC COMPOSITIONS

Composition 1 — Skin lotion

A lotion having the following formulation is prepared:

| | |
|---|---|
| Essence of lavender | 0.6 g |
| Witch hazel water | 10.0 g |
| Sorbitol (70%) | 4.0 g |
| Sodium salt of ethylenediamine tetraacetic acid | 0.1 g |
| Hydrogenated ricin oil polyoxyethylenated with 60 moles of ethylene oxide | 0.8 g |
| Preservative agent | 0.3 g |
| Acellular planktonic extract | 0.6 g |
| Distilled water, q.s.p. | 100.0 g |

The composition of the preservative agent is as follows:

| | |
|---|---|
| The amine salt of benzoic acid and ortho- and para-hydroxy benzoic acid | 0.1 g |
| Benzoic acid | 0.2 g |

The above lotion is prepared in the following manner: The perfume (essence of lavender of witch hazel water) is peptized and the hydrogenated ricin oil polyoxyethylenated with 60 moles of ethylene oxide is added thereto. To the resulting mixture there is added an aqueous solution containing the preservative agent, the sorbitol and the sodium salt of ethylene diamine tetraacetic acid. Finally the acellular planktonic extract is added after which the composition is completed by the addition of sufficient distilled water to bring the total weight thereof to 100 g.

Composition 2 — Skin cream

A beauty cream having the following formulation is prepared:

| | |
|---|---|
| Glyceryl esters of fatty acids (C$_8$ - C$_{14}$) | 10.0 g |
| Isopropyl myristate | 2.0 g |
| Cetyl alcohol | 6.2 g |
| Stearic acid | 2.0 g |
| Polyethylene glycol (MW 300) | 2.0 g |
| Ethylene glycol stearate oxyethylenated with 40 moles of ethylene oxide | 2.3 g |
| Sorbitol monostearate | 2.7 g |
| Carboxymethyl cellulose | 0.3 g |
| Triethanolamine | 0.35 g |
| Preservative agent | 0.3 g |
| Perfume | 0.4 g |
| Acellular planktonic extract | 0.6 g |
| Water, q.s.p. | 100.0 g |

The composition of the preservative agent is the same as that employed in Composition 1.

The above skin cream is prepared in the following manner:

At a temperature of 70°-80° C, the above ethers, alcohols and fatty acids, as well as the polyethylene glycol, are emulsified with the water containing the triethanolamine and the preservative agent. To the resulting emulsion, there is added the carboxymethylcellulose previously dissolved in a little water. The resulting product is then cooled while agitating the same and to the resulting cooled product there are added the perfume and the acellular planktonic extract. Thereafter the remaining water is added with agitation.

What is claimed is:

1. A cosmetic composition for application to the skin consisting essentially of an aqueous solution or suspension or an accellular planktonic product consisting essentially of the cytoplasmic content of cellular planktonic membranes of sulfurous spa origin, said planktonic product being an emollient and being present in an effective amount to produce an emollient or softening effect on the skin.

2. The cosmetic composition of claim 1 present in the form of a lotion or a cream.

3. The cosmetic composition of claim 1 present in the form of a cream wherein said acellular planktonic product is in the form of a lyophilizate coated with a cosmetic fatty body applicable to the skin.

4. The cosmetic composition of claim 1 wherein said planktonic product is present in an amount between 0.3 and 1 percent of the total weight of said composition.

5. A cosmetic composition for application to the skin consisting essentially of an aqueous solution or suspension of an acellular planktonic product consisting essentially of the cytoplasmic content of cellular planktonic membranes of sulfurous spa origin and the ruptured cellular planktonic membranes thereof, said planktonic product being an emollient and beng present in an effective amount to produce an emollient or softening effect on the skin.

6. The cosmetic composition of claim 5 in the form of a lotion or a cream.

7. The cosmetic composition of claim 5 in the form of a cream wherein said acellular planktonic product is in the form of a lyophilizate coated with a cosmetic fatty body applicable to the skin.

8. The cosmetic composition of claim 5 wherein said planktonic product is present in an amount between 0.3 and 1 percent of the total weight of said composition.

* * * * *